United States Patent [19]

Mick et al.

[11] Patent Number: 5,790,307
[45] Date of Patent: Aug. 4, 1998

[54] STEREOTACTIC ADAPTER AND PROCEDURE FOR ITS USE

[75] Inventors: Franz Mick, Friedland; Bernhard Ludwig Bauer, Marburg; Joachim Luber, Essingen; Arvids Mackevics, Aalen, all of Germany

[73] Assignee: Carl Zeiss Stiftung, Brenz, Germany

[21] Appl. No.: 420,967

[22] Filed: Apr. 13, 1995

[30] Foreign Application Priority Data

Apr. 13, 1994 [DE] Germany .......................... 44 12 605.0

[51] Int. Cl.[6] ............................. G02B 21/00; F16L 3/00
[52] U.S. Cl. .......................... 359/382; 359/383; 359/384; 248/123.1; 248/181.1
[58] Field of Search .................... 359/382, 383, 359/384; 248/121, 122, 123.1, 124, 280.1, 281.1

[56] References Cited

U.S. PATENT DOCUMENTS

| | | | |
|---|---|---|---|
| 4,264,167 | 4/1981 | Plummer | 354/62 |
| 4,273,431 | 6/1981 | Farmer et al. | 354/59 |
| 4,364,629 | 12/1982 | Lang et al. | 359/377 |
| 4,639,772 | 1/1987 | Sluyter et al. | 358/98 |
| 5,071,241 | 12/1991 | Brock | 359/390 |
| 5,310,674 | 5/1994 | Weinreb et al. | 435/293 |

*Primary Examiner*—Thong Nguyen
*Assistant Examiner*—Mohammad Y. Sikder

[57] ABSTRACT

A stereotactic adapter on which a surgical therapeutic and/or diagnostic instrument is reproducibly mounted and attached to a surgical microscope that can be positioned in several spatial degrees of freedom. A position recognition system integrated in the surgical microscope permits safe positioning of the instrument used, given the geometric arrangement and the geometric dimensions of the surgical microscope, the adapter, and the instrument.

17 Claims, 5 Drawing Sheets

STEREOTACTIC ADAPTER AND PROCEDURE FOR ITS USE

BACKGROUND OF THE INVENTION

1. Field of the Invention

The present invention relates to a stereotactic adapter for mounting a surgical therapeutic and/or diagnostic instrument on a surgical microscope which is attached to a motorized carrier system and positioned by it. The present invention also relates to a procedure for the operation of an adapter of this type.

2. Relevant Prior Art

A wide variety of devices for the defined positioning of surgical therapeutic and/or diagnostic instruments are known in computer-aided stereotactic surgery. U.S. Pat. Nos. 5,228,429; 5,078,140; 5,142,930; 5,050,608; and 5,332,181 describe relevant examples.

In the devices described in these patents, various surgical therapeutic and/or diagnostic instruments such as endoscopes, biopsy needles, surgical microscopes, etc., are mounted on a multi-joint carrier system comprising appropriate angle encoders for the individual joints that are evaluated by a central control unit. In some cases, the carrier systems also provide drives for the shafts of the different joints. Thus, the carrier systems allow defined positioning of the instruments mounted on them within the respective coordinate system of the apparatus and in several spatial degrees of freedom.

If stereotactic surgery is to be performed on a patient using these devices with surgical therapeutic and/or diagnostic instruments mounted on them, it is first necessary to correlate the coordinate system of the patient with the coordinate system of the device to ensure subsequent defined positioning of the instrument used. In U.S. Pat. No. 5,228,429 this is implemented in such a way that the tip of the endoscope to be positioned is brought into contact with the parts of the body to be treated and several of these probing procedures are performed to deduce the position or the size of the part of the body concerned. It is obvious that this procedure of referencing the different coordinate systems, which is essential for the stereotactic use of the endoscope, has inherent risks for the patient, especially if this referencing procedure is to be performed in the area of the patient's brain.

A correlation is performed not only between the patient and the instrument coordinate systems, but also with diagnostic images obtained pre-operatively, i.e., with the relevant image coordinate system, if this image-based information also is to be used for system control.

SUMMARY OF THE INVENTION

The object of the present invention is to create a device and a procedure that avoids the above disadvantages and allows the safe stereotactic use of various therapeutic and/or diagnostic instruments that can be positioned by means of a motorized carrier system.

According to the invention, a surgical microscope is provided with a stereotactic adapter on which the surgical therapeutic and/or diagnostic instrument is mounted in a defined, relative position. The surgical microscope itself is attached to a motorized carrier system which allows the positioning of the surgical microscope in several spatial degrees of freedom. Thus, the adapter according to the invention ensures the reproducible and known geometric arrangement of the surgical therapeutic and/or diagnostic instruments used on the microscope. In view of the known geometric dimensions of the surgical microscope, the adapter and the instrument used, the adapter according to the invention now allows the safe, defined positioning of the surgical therapeutic and/or diagnostic instrument using the motorized carrier system. A central control unit, e.g., a workstation, continuously determines and updates the coordinates of both the target area of the respective instrument from the known geometric information and the information supplied by the encoders of the motorized carrier system.

In addition to the advantage that the referencing procedure correlating the different coordinate systems and thus also the instrument used now no longer puts the patient at risk, another asset offered by the use of the stereotactic adapter according to the invention lies in the fact that it enables the surgeon to observe details of interest through the surgical microscope. This allows, for example, the rapid visual inspection of a small incision intended for the insertion of an endoscope.

The referencing procedure correlating the surgical therapeutic and/or diagnostic instrument is carried out, for example, by the appropriate positioning or optical referencing of the surgical microscope as described in U.S. Pat. No. 5,359,417, which issued Oct. 25, 1994, and is hereby incorporated herein by reference. Thus, the navigation possibilities offered by the surgical microscope with its detectors and the positional recognition system on an optical basis are utilized in a beneficial manner. With the aid of the data thus obtained and the known geometric dimensions of the surgical microscope, the instrument and the adapter, the referencing procedure is performed for the instrument used.

Instead of this positional recognition system on an optical basis, suitable acoustic positional recognition systems can also be used that allow with high precision the three-dimensional determination of both the patient's coordinates and the coordinates of the surgical microscope with high precision.

BRIEF DESCRIPTION OF THE DRAWINGS

Further advantages and details of the present invention and the procedure according to the invention will become apparent from the following description of preferred embodiments with reference to the accompanying drawings, in which.

DETAILED DESCRIPTION OF PREFERRED EMBODIMENTS

Figure 1:
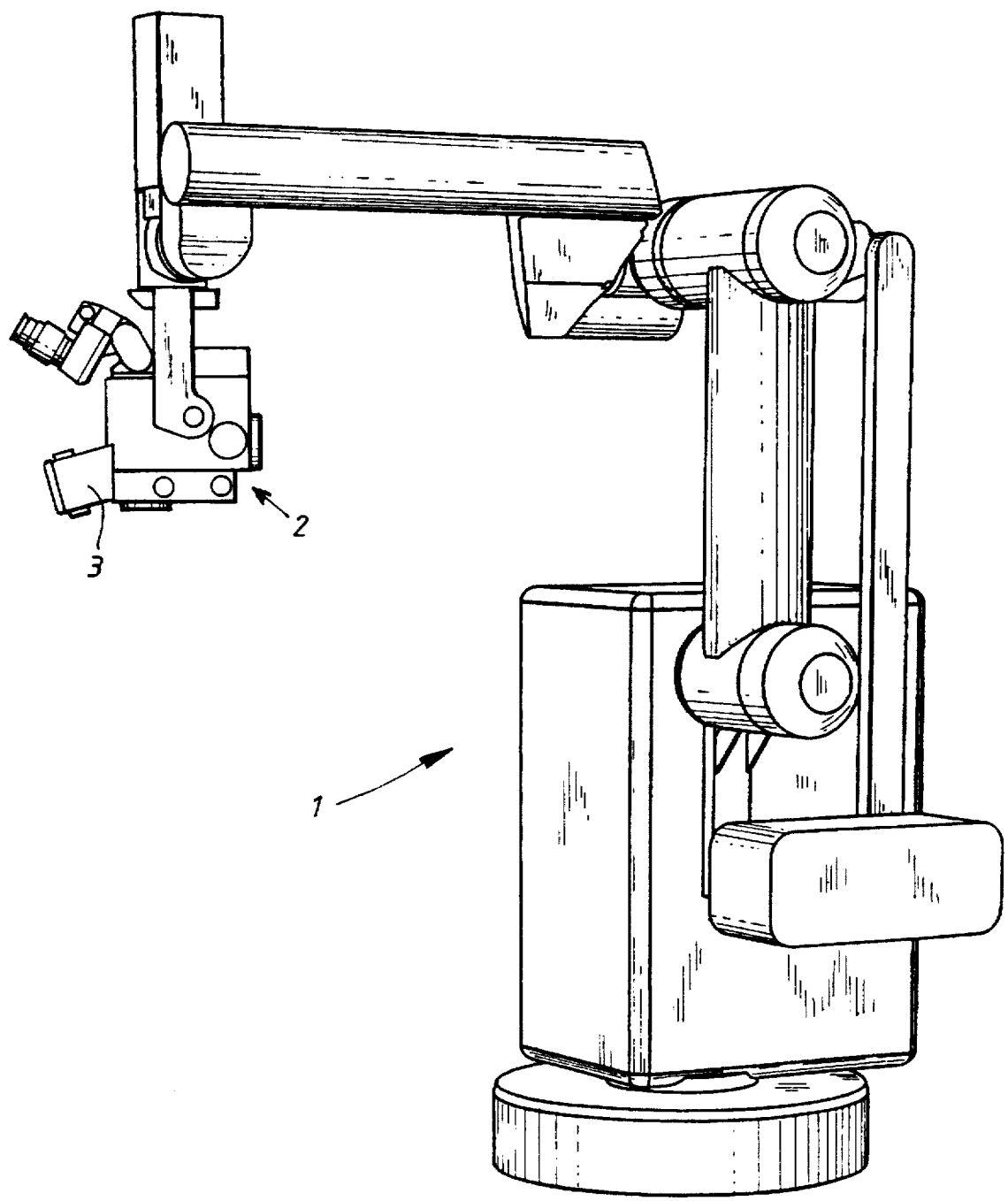
FIG. 1: shows a schematic diagram of the stereotactic adapter according to the invention, mounted on a suitable surgical microscope, positioned by means of a motorized carrier system.

FIG. 1 shows an embodiment of the stereotactic adapter (3) according to the invention, which is mounted on a suitable surgical microscope (2). The surgical microscope (2) itself is mounted on a motorized carrier system (1) such as that known, for example, from U.S. Pat. No. 5,332,181, which is hereby incorporated herein by reference.

The motorized carrier system (1) features a number of components connected with each other via joints, with the joints of the individual axes being driven by a motor (5) and including one or several angle encoders (6). The motorized carrier system (1) allows the defined motorized positioning of the instruments mounted on it up in to six spatial degrees of freedom with high positioning accuracy.

The angle encoders integrated in each joint of the motorized carrier system (1) supply information regarding the current position of the respective joints to a central control unit which, in the embodiment shown, is accomodated in the base of the motorized carrier system (1) and is therefore not visible in FIG. 1. On the basis of the known geometric data of the motorized carrier system and the data provided by the encoders, the current position of the surgical microscope mounted on the system and/or the position of the current field of view can always be determined.

The above-mentioned U.S. Pat. No. 5,332,181, gives a detailed description of the motorized carrier system (1).

A surgical microscope (2) that is suitable in a beneficial manner for this type of mounting or this type of application is known from the above-mentioned U.S. Pat. No. 5,359,417. This surgical microscope features detectors for the acquisition of such optical system data as magnification and focus position, and an integrated positional recognition system (7) on an optical basis, ensuring that, via the central control unit, the exact spatial position and orientation of both the surgical microscope (2) and the field of view observed are always known.

As already indicated above, instead of the integrated optical positional recognition system, for example, an acoustic positional recognition system on an ultra-sound basis can also be used according to the invention. Systems of this type are known as 3D digitizers.

The surgical microscope (2) also comprises a superimposing device that allows various images obtained during pre-operative diagnostic procedures or images suitably processed in some other way to be projected onto the microscope image. The superimposition of these images on the field of view observed constitutes an orientation aid for the surgeon during surgery.

According to the invention, the surgical microscope (2) carries the stereotactic adapter (3), which allows the clearly reproducible mounting of a surgical therapeutic and/or diagnostic instrument on the surgical microscope (2) and hence on the motorized carrier system (1). In FIG. 1, the stereotactic adapter (3) according to the invention holds a schematically depicted endoscope (8) as an example of a surgical therapeutic and/or diagnostic instrument.

The stereotactic adapter (3) according to the invention now allows the computer-aided use of a surgical microscope (2) in conjunction with a surgical therapeutic and/or diagnostic instrument, with the motorized carrier system being capable of allowing a defined spatial positioning in at least three spatial degrees of freedom. The embodiment of the motorized carrier system (1) shown is known from U.S. Pat. No. 5,332,181 and even allows positioning in a total of six spatial degrees of freedom, i.e., three translational and three rotational degrees of freedom.

The utilization of the optical referencing procedure for the surgical microscope now also permits the non-contact referencing of the instrument used and thus its safe stereotactic use.

Figure 2:
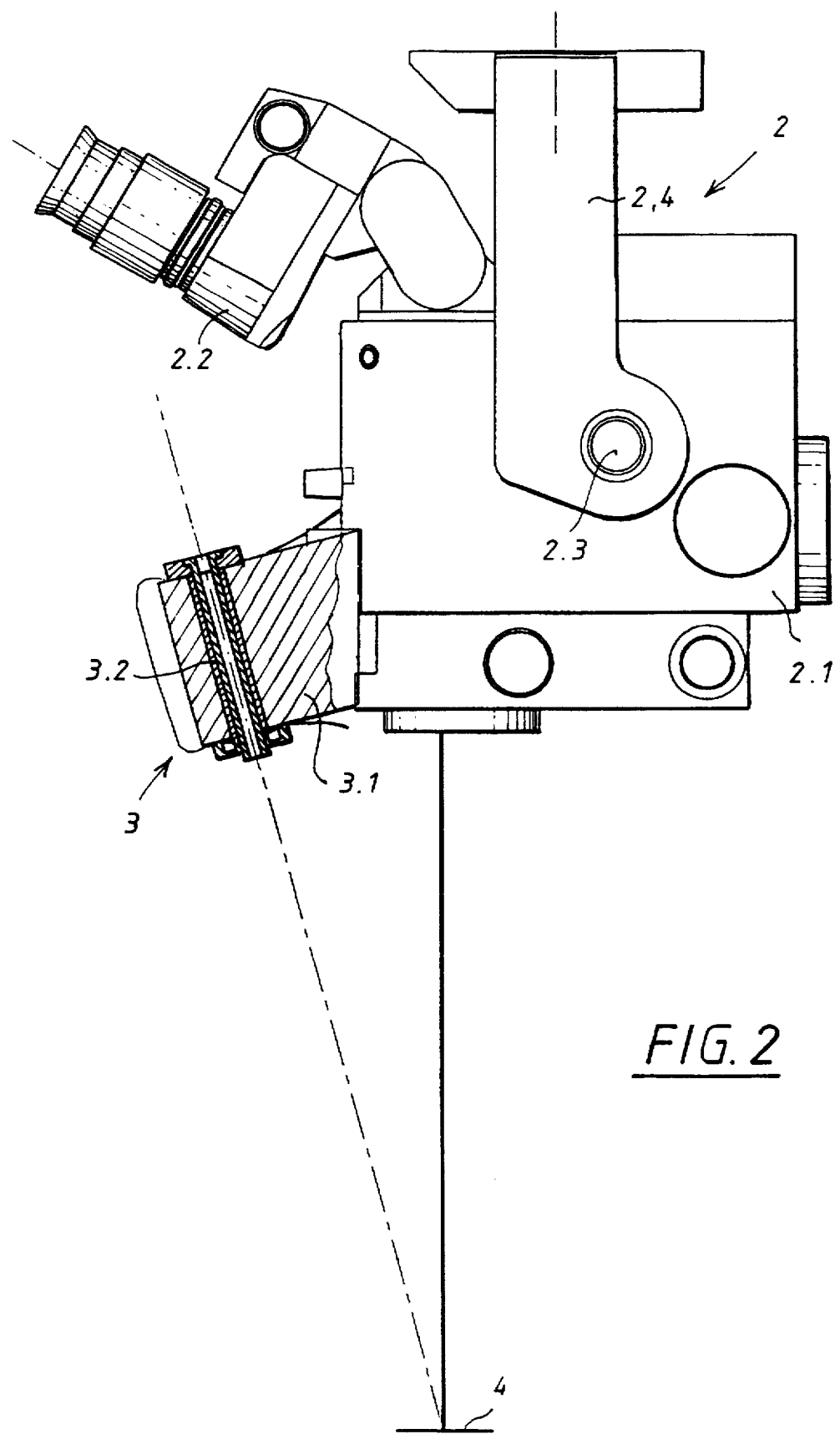
FIG. 2: shows a lateral view of the surgical microscope including the stereotactic adapter shown in FIG. 2.

The design of the stereotactic adapter according to the invention is explained in more detail using FIG. 2, which shows a lateral view of the surgical microscope (2) illustrated in FIG. 1 including a partial section of the adapter (3) according to the invention. The surgical microscope (2) attached to the motorized carrier system via a connecting component (2.4) includes the microscope body housing (2.1) which accommodates the complete optical system including detectors and the positional recognition system (7) (shown schematically). More details on the design of the surgical microscope (2) to be preferably used are provided in U.S. Pat. No. 5,359,417. On the top of the microscope body housing (2.1) a familiar binocular tube (2.2) is mounted which allows tilting relative to the microscope body housing (2.1) of the surgical microscope (2). The surgical microscope (2) also features a flexible interface connecting component (2.4).

The stereotactic adapter (3) according to the invention is mounted on the lower part of the microscope body housing (2.1) of the surgical microscope (2). This requires a rigid connection between the adapter (3) and the surgical microscope (2), as only then will defined mounting of the components relative to each other be ensured.

Figure 3:
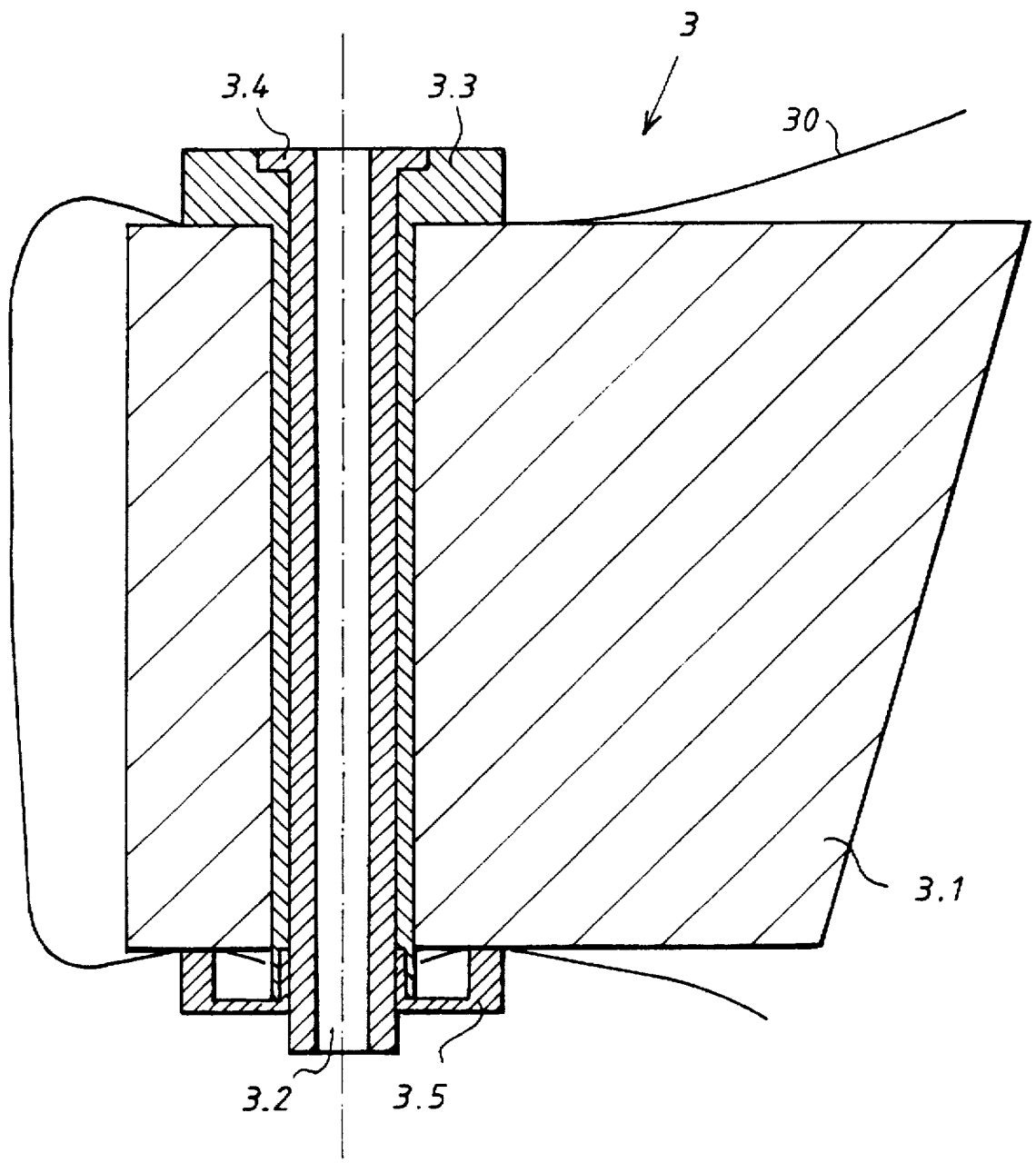
FIG. 3: shows a section through the stereotactic adapter shown in FIG. 2.

The connection between the surgical microscope (2) and the adapter (3) may be of a permanent or non-permanent nature. It is only important that the connection itself be rigid. A possible form of connection would be a screw connection, etc. The stereotactic adapter (3) mounted on the surgical microscope (2) consists of a basic body (3.1) with a cylindrical duct (3.2) in which the surgical therapeutic and/or diagnostic instrument such as the schematically depicted biopsy needle (3.3) can be inserted. The following description of FIG. 3 provides further information on the design of the adapter according to the invention.

The stereotactic adapter (3) is mounted on the surgical microscope in such a way that the cylindrical duct (3.2) and hence also the surgical therapeutic and/or diagnostic instrument guided therein in thiscase, the biopsy needle (3.3),is pointing in a defined, known direction. The field-of-view plane observed ((4) in FIG. 2) and the surgical therapeutic and/or diagnostic instrument or its target area are thus reproducibly oriented relative to each other by the adapter (3). Once the exact position of the field-of-view plane has been determined as described in U.S. Pat. No. 5,359,417, the coordinates of the target area of the instrument used are also known to the central control unit.

To determine the target area, it remains to be established how far the instrument used is inserted in the cylindrical duct and what the dimensions of this instrument are. If, for example, an endoscope is used as the surgical therapeutic and/or diagnostic instrument in the stereotactic adapter, the target area of the instrument is defined as the point of instrument entry on the patient.

The geometric data of the instrument inserted in the stereotactic adapter required for the exact determination of the target area can now be made available to the central control unit in different ways. One possibility, for example, is that the user manually enters this geometric data of the instrument via an input interface. As an alternative, this information can also be supplied to the central control unit in an automated manner. To achieve this, the adapter features a code recognition system that allows the automated, clear identification of the instrument used. This identification information is transmitted to the central control unit, which stores the geometric data of a number of different instruments, making it possible to assign the correct instrument to the identification information supplied.

Suitable code recognition systems are, for example, familiar optical coding systems (3.4) such as the bar code system or similar systems. Also possible, however, is the use of magnetic code systems, etc.

FIG. 3 shows a further enlarged lateral view of a section through the adapter (3) according to the invention. The basic body (3.1) of the adapter (3) provides a cylindrical duct (3.2) in which the instrument, e.g., an endoscope, is inserted. A number of cylindrical sleeves with different cylinder diameters and sleeve lengths, etc., are available for the cylindrical duct in the adapter. In FIG. 3, two of these sleeves (3.3, 3.4) have been inserted in the cylindrical duct (3.2) of the adapter (3). The sleeves (3.3, 3.4) with different diameters are used as adapter components to allow the insertion of various instruments in a single adapter. These adapter components permit different instruments such as endoscopes and biopsy needles or different endoscopes with different telescope diameters to be inserted in the same adapter in a beneficial manner, making the use of separate adapters unnecessary. Mounting of the matching sleeves is all that is needed before the insertion of the instrument to be used. In the embodiment shown in FIG. 3, a locking component (3.5) is provided on the underside of the adapter and used for the secure attachment of the sleeves (3.3, 3.4) inserted.

Further locking components are required to prevent the instrument inserted in the adapter from falling out and to guarantee the defined position of the instrument relative to the adapter or the surgical microscope. For this, the instrument can, for example, be screwed onto the adapter. The adapter (3) has at least one adjustable mechanical end stop that allows movement of the surgical instrument in the cylindrical duct in the adapter in the longitudinal direction of the duct to a defined position.

FIG. 3 also shows part of a drape (30) used to cover both the surgical microscope and the adapter (3) during surgery. The drape (30) features openings where the instrument concerned extends into, or protrudes from the adapter. In addition, the drape must be protected against slipping to ensure the correct position of these two openings. For example, the drape (30) can be suitably clamped onto the adapter using the sleeves (3.3, 3.4) and/or locking components (3.5).

For reasons of sterility, it is also beneficial that the sleeves used for adaptation to various instrument geometries can be sterilized. For example, the sleeves can be provided with a sterile cover or made from a material allowing simple sterilization in an autoclave.

Figure 4:
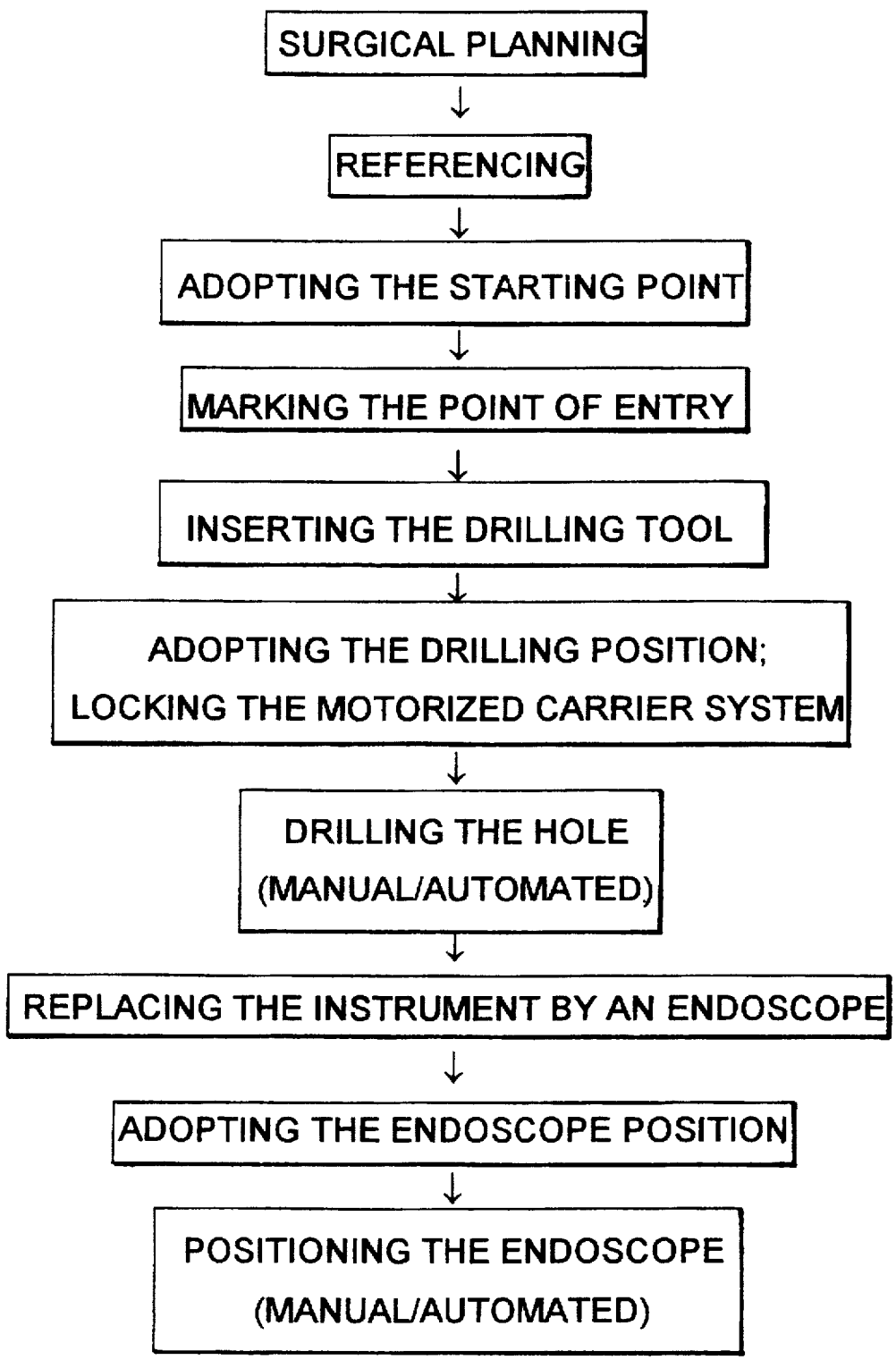
FIG. 4: shows a flow chart showing the procedural sequence to be followed for a procedure according to the invention using the stereotactic adapter shown in FIGS. 1–3.

The flow chart shown in FIG. 4 describes a possible procedure for the operation of the adapter according to the invention in conjunction with a drill and an endoscope during brain surgery.

Before the operation, the surgeon performs the surgical planning procedure on the central control unit. Using the diagnostic data generated pre-operatively, e.g., CT images, he or she defines the point of endoscope entry on the patient.

Subsequently, the optical referencing procedure correlating the coordinate systems of the patient, the apparatus and the image used with each other is performed using the surgical microscope described in U.S. Pat. No. 5,359,417. For this, for example, three so-called markers on the patient are measured in successive calibration measurements using the optical positional recognition system. Using the information obtained from these calibration measurements, the central control unit correlates the different coordinate systems: equipment coordinate system, image coordinate system, and patient coordinate system. Afterward, the motorized carrier system moves the surgical microscope to the starting point stipulated in the surgical planning procedure, with the point of endoscope entry lying in the center of the field of view of the surgical microscope. At this stage of the procedure it is possible, for example, to superimpose the necessary drill hole on the patient on the field of view by projecting previously processed diagnostic images onto the microscope image. At the next stage of the procedure, the surgeon transmits the position or shape of the necessary drill hole to the skin of the patient by marking the patient's skin either manually or using a laser.

After the point of entry has been marked, the surgical microscope is moved for safety reasons to a safe distance from the patient and the necessary drilling tool is inserted in the adapter. The drilling position is adopted and the motorized carrier system is locked in this position. After this, it is possible to produce the drill hole either in a manual - guided by the adapter - or an automated manner at the point marked. In the latter case, the motorized carrier system and the surgical microscope mounted thereon, including the adapter and the drill, are re-oriented, followed by the stereotactic drilling of the drill hole required. After this stage of the procedure, i.e., the drilling of the hole in a stereotactically automated or manual manner, the drill is removed from the adapter and an endoscope or a different medical therapeutic and/or diagnostic instrument is inserted in the adapter.

Subsequently, the motorized carrier system moves the endoscope into the position required. The following insertion or positioning of the endoscope or any other instrument used can be performed in a manual or, again, automated manner via the motorized carrier system.

Before the instrument is manually inserted in the patient, the motorized carrier system moves the surgical microscope and the adapter to the distance or position which is necessary to ensure that, when the instrument is manually inserted, the desired target point is reached when the instrument reaches a mechanical stop in the adapter. After the motorized carrier system has adopted this position, it maintains this position by locking the necessary brakes until the surgeon has manually inserted the instrument.

For the motorized carrier system to be able to assume this position, the central control unit not only requires the coordinate information specified during the surgical planning procedure, but also the geometric data on the adapter or the instrument that was transmitted to the central control unit either in a manual or an automated manner.

As an alternative to the manual stereotactic insertion of the instrument used, it is also possible, however, to insert the endoscope with the guidance by the motorized carrier system in the drill hole on the patient in an automated manner. For this, the endoscope is connected with the surgical microscope or the adapter in a fixed or defined manner and locked appropriately in position. Subsequently, the motorized carrier system moves the endoscope in a defined manner along the pre-planned pathway, the position of the instrument or its tip is always known to the central control unit.

When the instrument is inserted using this automated manner, it is beneficial to provide a safety device which automatically stops the movement of the instrument if any obstacles are encountered along the pathway and which does not allow any further positioning of the instrument until an acknowledgement has been given by the surgeon. To achieve this, familiar Doppler systems can be used.

Figure 5:
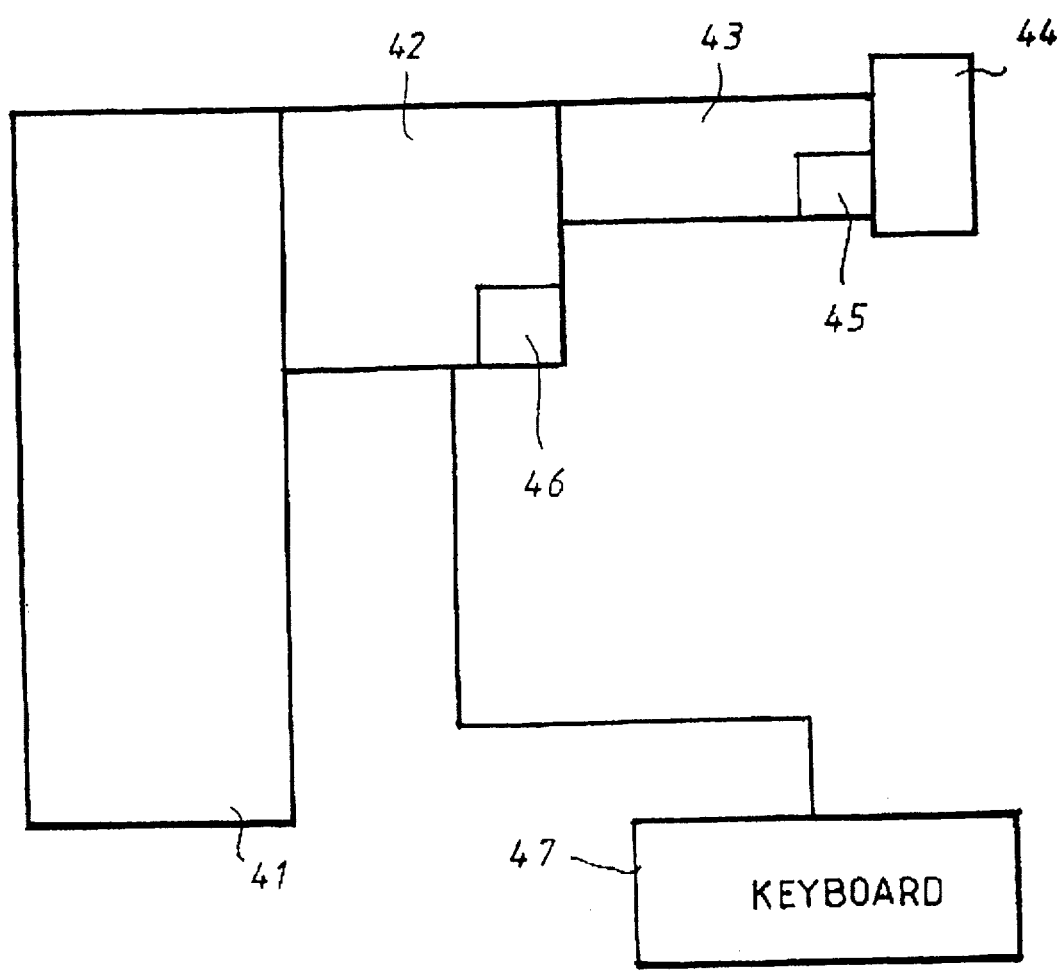
FIG. 5: shows a schematic view of the stereotactic adapter according to the invention with a surgical microscope, a surgical instrument and a motorized carrier system.

FIG. 5 shows a complete arrangement according to the invention. A motorized carrier system (41) supports and positions an operation microscope (42), which has an acoustic position recognition system (46) fitted to it. This position recognition system also may be an optical system, as shown schematically in FIGS. 1 and 2. A stereotactic adapter (43) is fitted to the operation microscope (42), for supporting a surgical instrument (44) mounted on the stereotactic adapter (43). The surgical instrument (44) may be, interchangeably, an endoscope, or a biopsy needle, or other surgical instrument.

A code recognition system (45), operating on a magnetic coding principle, is fitted to the stereotactic adapter (43) to automatically identify the surgical instrument used. A keyboard (47) provides an input interface to the operation microscope (42) for providing manual identification of the surgical instrument (44) used.

I claim:

1. Apparatus comprising:
   a surgical microscope (2),
   a positional recognition system fitted to said surgical microscope (2),
   a motorized carrier system (1) attached to said surgical microscope (2) for positioning said surgical microscope (2) in at least three degrees of spatial freedom,
   central control unit for controlling said motorized carrier system (1), and
   a stereotactic adapter (3) on said surgical microscope (2) for ensuring reproducible mounting of a surgical instrument on said surgical microscope (2).

2. Apparatus according to claim 1, comprising code recognition means fitted to said adapter (3) or said surgical microscope (2) for code identification of said surgical instrument and for transmitting code information to said central control means, wherein said central control means comprises identification means for identifying said surgical instrument and providing geometric information concerning said surgical instrument using said code information.

3. Apparatus according to claim 2, wherein said code recognition means comprises an optical coding system.

4. Apparatus according to claim 2, wherein said code recognition means comprises a magnetic coding system.

5. Apparatus according to claim 1, wherein said central control means comprises an input interface for manual identification of said surgical instrument.

6. Apparatus according to claim 1, wherein said surgical instrument comprises an endoscope.

7. Apparatus according to claim 1, wherein said surgical instrument comprises a biopsy needle.

8. Apparatus according to claim 1, wherein said surgical microscope has a field-of-view center and includes a housing (2.1), said adapter (3) further comprising mounting means for removably mounting said adapter to said housing (2.1) and cylindrical duct (3.2) into which said surgical instrument is insertable, said cylindrical duct having an axis that points towards said field-of view center.

9. Apparatus according to claim 1, wherein said positional recognition system comprises an optical system.

10. Apparatus according to claim 1, wherein said positional recognition system comprises an acoustic system.

11. Method for operation of a stereotactic adapter that enables reproducible mounting of a surgical instrument on a surgical microscope (2), said sterostactic adapter (3) being attached to said surgical microscope (2) and said surgical microscope (2) being attached to a motorized carrier system (1) that is controlled by a central control unit and enables positioning of said surgical microscope (2) in at least three spatial degrees of freedom, comprising:

identifying said surgical instrument by said central control unit, correlating coordinate systems of a patient, said microscope (2) and said motorized carrier system (1) with each other via a positional recognition system integrated in said surgical microscope (2), and moving said surgical microscope (2) by said motorized carrier system (1) to a starting point determined by said central control unit in dependence on the surgical instrument being used.

12. Method according to claim 11, further comprising manually inserting said surgical instrument in said patient.

13. Method according to claim 11, further comprising inserting by motorized means, said surgical instrument in said patient.

14. Method according to claim 12, further comprising defining a target position via a mechanical end stop on said adapter when said instrument is manually inserted.

15. Method according to claim 13, further comprising controlling said motorized insertion by said central control unit.

16. Method according to claim 11, wherein said identifying step further comprises identifying said instrument in an automated manner using a code recognition system.

17. Method according to claim 11, wherein said identifying stop further comprises identifying said instrument by manual input of data at an input interface on said central control unit.

* * * * *

UNITED STATES PATENT AND TRADEMARK OFFICE
CERTIFICATE OF CORRECTION

PATENT NO. : 5,790,307
DATED : August 4, 1998
INVENTOR(S) : Joachim Luber; Arvids Mackevics; Franz Mick & Bernhard Ludwig Bauer It is certified that error appears in the above-identified patent and that said Letters Patent is hereby corrected as shown below:

On the cover page
cancel "[75] Inventors: Franz Mick, Friedland; Bernhard Ludwig Bauer, Marburg; Joachim Luber, Essingen; Arvidz Mackevics, Aalen, all of Germany"

insert--[75] Inventors: Joachim Luber, Essingen; Arvidz Mackevics, Aalen; Franz Mick, Friedland; Bernhard Ludwig Bauer, Marburg, all of Germany --.

Signed and Sealed this

Eighth Day of February, 2000

Attest:

Q. TODD DICKINSON

Attesting Officer

Commissioner of Patents and Trademarks